United States Patent [19]

Chu et al.

[11] Patent Number: 5,776,490
[45] Date of Patent: Jul. 7, 1998

[54] COMPLEX PROTEIN-WALLED MICROCAPSULES CONTAINING LIPID-WALLED MICROCAPSULES AND METHOD FOR PRODUCING SAME

[75] Inventors: Fu-Lin E. Chu, Williamsburg, Va.; Sureyya Ozkizilcik, Baltimore, Md.

[73] Assignee: The Center for Innovative Technology, Herndon, Va.

[21] Appl. No.: 590,701

[22] Filed: Jan. 26, 1996

[51] Int. Cl.$^6$ .................................................. A61K 9/50
[52] U.S. Cl. .......................... 424/451; 424/452; 424/489; 424/491; 424/450; 428/402.2; 428/402.24; 264/4.32; 264/12
[58] Field of Search .................... 424/451, 452, 424/455, 450, 489, 490, 491, 499; 428/402.2, 402.24; 264/4.32, 12

[56] References Cited

U.S. PATENT DOCUMENTS

| | | | |
|---|---|---|---|
| 3,116,206 | 12/1963 | Brynko | 167/83 |
| 4,273,672 | 6/1981 | Vassiliades | 252/316 |
| 4,349,530 | 9/1982 | Royer | 424/19 |
| 4,627,850 | 12/1986 | Deters | 604/892 |
| 4,798,786 | 1/1989 | Tice et al. | 424/93 |
| 4,921,705 | 5/1990 | Arai | 424/450 |
| 5,026,559 | 6/1991 | Eichel | 424/458 |
| 5,069,936 | 12/1991 | Yen | 264/4.1 |
| 5,151,264 | 9/1992 | Samain | 424/1.1 |
| 5,198,227 | 3/1993 | Batista | 424/463 |
| 5,211,980 | 5/1993 | Cox | 426/601 |
| 5,227,298 | 7/1993 | Weber | 435/178 |
| 5,248,772 | 9/1993 | Siiman | 536/112 |
| 5,362,424 | 11/1994 | Lee | 264/4.3 |
| 5,401,515 | 3/1995 | Woodard | 424/475 |

*Primary Examiner*—James M. Spear
*Attorney, Agent, or Firm*—Whitham, Curtis & Whitham

[57] ABSTRACT

Complex protein walled microcapsules (40) incorporate lipid-walled microcapsules (48) that include constituents to be retained in the presence of hydration such as water soluble vitamins and minerals. The protein walled microcapsules (40) are cross-linked, and include constituents (46) that are excluded from the lipid-walled microcapsules (48) and which are leachable from the protein walled microcapsules upon hydration. Other constituents (42 and 44), such as high molecular weight compounds and particulates may also be included in the protein walled microcapsules (40). Preferably, these other constituents (42 and 44) are chosen to be retained within the protein-walled microcapsules (40) upon hydration. In a preferred embodiment, the complex protein-walled microcapsules are used as a fish larvae diet, wherein low molecular weight constituents, such as amino acids, that are incorporated into the protein-walled microcapsule but excluded from the lipid-walled microcapsule, are chosen for use as phagostimulants and attractants. They are leached out from the protein-walled microcapsule upon hydration. Nutrients such as vitamins and minerals are retained in the lipid-walled capsules of the complex protein-walled microcapsules. Larvae are stimulated from the leached phagostimulants and ingest the complex protein walled microcapsule as food, wherein the encapsulated water soluble vitamins and minerals, as well as the protein itself serve as nutrients for the larvae.

3 Claims, 3 Drawing Sheets

COMPLEX PROTEIN-WALLED MICROCAPSULES CONTAINING LIPID-WALLED MICROCAPSULES AND METHOD FOR PRODUCING SAME

BACKGROUND OF THE INVENTION

1. Field of the Invention

The invention is generally related to two component microcapsules which include lipid-walled microcapsules that are contained within complex, cross-linked protein-walled microcapsules. More particularly, the invention pertains to microcapsules for delivering drugs and/or nutrients to animals, and which has particular application to aquaculture.

2. Description of the Prior Art

Despite the difficulties involved in successfully promoting marine fish larvae to accept an artificial diet as first food, various microbound, microcoated and microencapsulated diets have been developed for the culture of marine fish larvae. While microbound diets have found wide spread use in the culture of larval marine organisms, excessive losses of low molecular weight and water soluble nutrients due to leaching has been consistently reported as a problem for microbound diets. For example, Lopez-Alvarado et al., *Aquaculture* 122:335–346, 1994, has reported that binding crystalline amino acids within alginate, carrageenan or zein particles resulted in 80–90% loss of amino acids within minutes after immersion in water. The leaching typically results from the high surface area to volume ratio for the microbound diets, and results in the microbound diets having limited utility and in reduced water quality.

Microencapsulation has emerged as a vehicle of nutrient delivery that may potentially overcome the restraints associated with nutrient leaching and low water stability. Various microencapsulation techniques have been used in laboratory scale trials in the culture of marine larvae, including larval *Crassostrea virginica* (Chu et al., *Aquaculture* 64:185–197, 1987), *Penaeus vannamei* (Villamar et al., *Marine Biology* 115:635–642, 1993), *Penaeus japonicus* (Jones et al., *Aquaculture* 64:133–146, 1987), and *Solea* (Appelbaum, *Aquaculture* 49:209–221, 1985).

Lipid-walled capsules (LWC) are capable of retaining water soluble compounds such as vitamins and minerals. However, Langdon et al., *Aquaculture* 39:135–153, 1984, has reported that this type of capsule cannot deliver high nutrient loads to meet nutritional needs completely. Protein-walled capsules (PWC) and Ca-alginate microcapsules can be used to encapsulate bulk nutrients such as protein, lipid, and carbohydrates, however, they rapidly release low molecular weight and water soluble compounds upon hydration. Villamar et al., *Marine Biology* 115:635–642, 1993, reported a method for small scale production of complex alginate microcapsules that are capable of retaining both macro and micronutrients. However, exhaustive trials by the inventors of this patent application have shown that the acceptability of complex alginate microcapsules by striped bass larvae was extremely low. In six separate trials involving several thousands of larval striped bass, only a few larvae were found to contain alginate microcapsules in their guts.

U.S. Pat. No. 5,401,515 to Woodard, U.S. Pat. No. 5,198,227 to Batista, and U.S. Pat. No. 5,069,936 to Yen each disclose examples of capsules that are not complex in nature, they are non-crosslinked, and they have a uniform release pattern.

U.S. Pat. No. 5,248,772 to Siiman et al., U.S. Pat. No. 5,096,717 to Wirth et al., U.S. Pat. No. 5,151,264 to Samain et al., and U.S. Pat. No. 5,026,559 to Eichel show examples of different processes for making macro and micro capsules.

The concept of ionic gelation is disclosed in U.S. Pat. No. 5,362,424 to Lee et al., U.S. Pat. No. 5,227,298 to Weber et al., and U.S. Pat. No. 5,211,980 to Cox. This process is based on the hardening of Na-alginate upon contact with divalent cations (i.e., calcium) to form, for example, a Ca-alginate matrix. Gelatins are often included in these types of capsules for the purpose of forming a homogenous matrix. Gelatin does not crosslink in the calcium chloride solution. Ionic gelation does not result in formation of a cross-linked polymer. Because the microparticles or microspheres are not cross-linked, they deform rapidly in warm aqueous solutions.

Examples of cross-linked protein-walled microcapsules with lipid/oil cores can be found in U.S. Pat. No. 4,921,705 to Arai, U.S. Pat. No. 4,273,672 to Vassiliades, U.S. Pat. No. 4,349,530 to Royer, and U.S. Pat. No. 3,116,205 to Brynko.

SUMMARY OF THE INVENTION

It is an object of this invention to provide a complex microcapsule which incorporates lipid-walled capsules along with other dietary material in a cross-linked protein microcapsule.

It is another object of this invention to provide a complex diet that has the capability of gradually releasing low molecular weight attractants, such as free amino acids from the semi-permeable protein-walled capsules, to stimulate ingestion by larval fish, while retaining highly water soluble vitamins and minerals in the non-permeable lipid-walled capsules, thus preserving dietary content.

According to the invention, protein-walled microcapsules which incorporate lipid-walled capsules and/or other types of microcapsules are used for the delivery of drugs, nutrients, and other agents. These complex microcapsules have the advantage of having different release patterns associated with the cross-linked protein-walled and the type of capsules embedded within the cross-linked protein wall. The microcapsules have particular application in the delivery of dietary nutrients to marine fish and shellfish larvae, since they are capable of releasing feeding stimulants while retaining essential nutrients for growth of the organisms. The complex microcapsules are prepared by combining protein-, lipid-walled microcapsules containing associated constituents, and additional constituents to be retained in the cross-linked protein matrix in a liquid solution. The liquid solution is then atomized to form fine microparticles containing each of the different ingredients. The microparticulate character is retained by capturing the sprayed microparticles in a solution containing a cross-linking agent that rapidly crosslinks the protein matrix such that the lipid-walled microcapsules with associated constituents, as well as the additional constituents that are associated with the protein matrix become encapsulated in a micro sized capsule of crosslinked protein.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
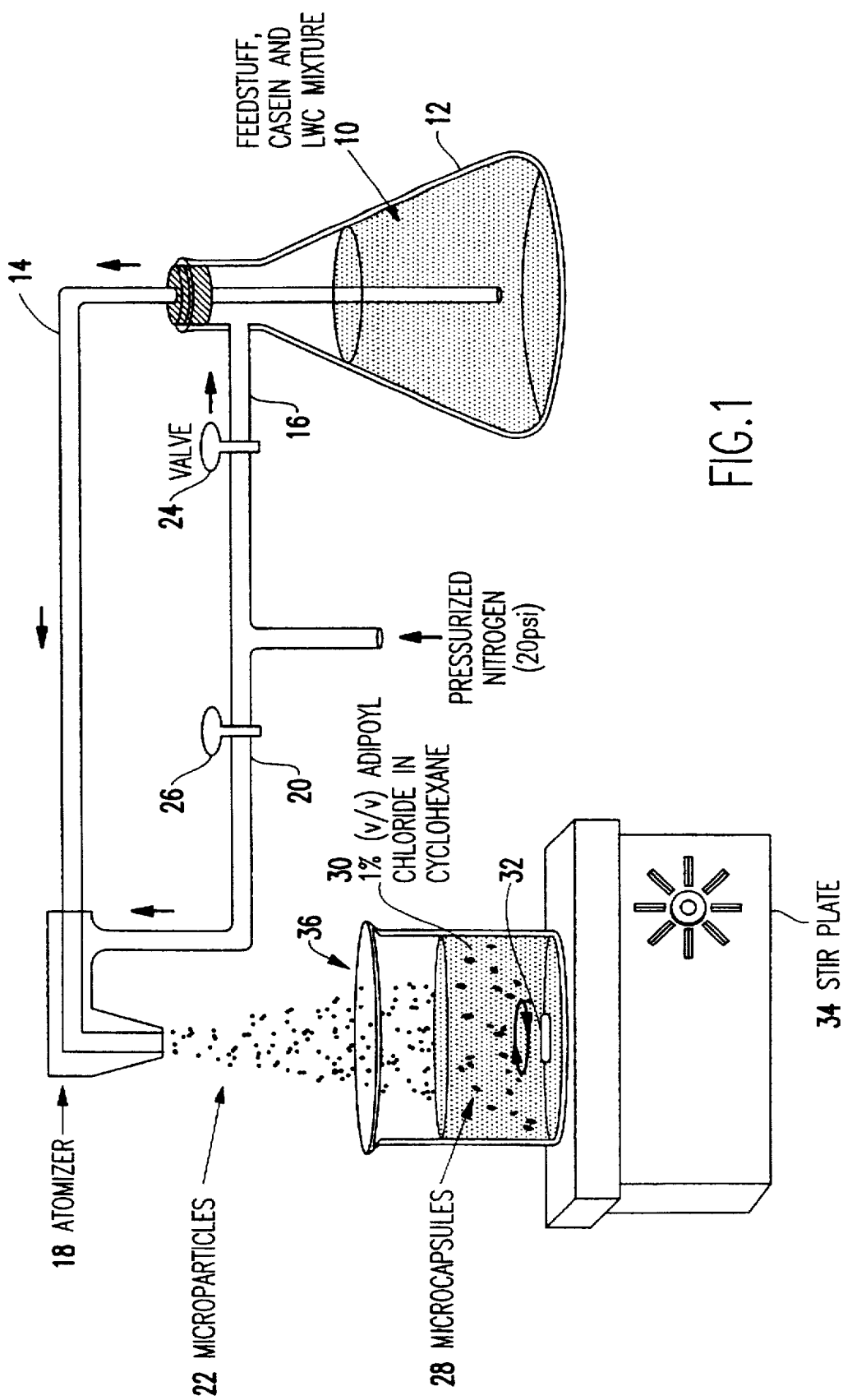
FIG. 1 is a schematic diagram of a laboratory scale apparatus used for producing complex microparticles according to the present invention.

The present invention is directed to the production of complex microparticles which include lipid-walled microcapsules that are encapsulated within a cross-linked, protein-walled microcapsule. The lipid-walled microcapsules are used to retain highly water soluble and/or low molecular weight constituents such as water soluble vitamins (e.g., vitamin C and Bs), antibiotics, drugs, minerals, peptides, and vaccines. The lipid character of the microcapsules allows the low molecular weight and water soluble constituents to be retained within the microparticles in the presence of water. The cross-linked, protein-walled capsules serves to retain the lipid-walled microcapsules as well as other constituents such as attractants and phagostimulants including amino acids, nucleotides, peptides, and sugars(mono- and di-saccharides). The cross-linked, protein-walled capsules are semi-permeable and permeable to water, and thus release constituents at a different and more rapid rate than the encapsulated lipid-walled microcapsules which are non-permeable to water when exposed to a water environment.

The combined entity is "complex" in that it includes two encapsulated entities, each with different release patterns. The complex microcapsules of the present invention are prepared by a) forming lipid-walled capsules with associated water soluble and low molecular weight species, b) combining these lipid-walled capsules with a cross-linkable protein material and any other constituents to be retained by a cross-linked matrix, c) atomizing the mixture of protein, constituents, and lipid-walled capsules to form microparticles, and d) collecting the microparticles in a solution containing a cross-linking agent, wherein the protein coating on the microparticles is rapidly cross-linked to produce a complex microcapsule with a cross-linked protein wall that encapsulates lipid-walled microcapsules.

In a particular embodiment of this invention, the complex microcapsules are employed as dietary material for marine and shellfish larvae. However, it should be understood that the microcapsules might also be used in other applications such as drug and/or nutrient delivery to humans or animals, etc. Thus, the studies described below, which are directed to the production and use of complex microcapsules for aquaculture diets, are for exemplary purposes only.

Materials and Methods

Preparation of Lipid-Walled Capsules

Lipid-walled capsules (LWC) can be prepared according to the methodology described in Langdon et al., *Aquaculture*, 39:135–153 (1984). For example, the lipid-walled material can be prepared by dissolving 5 g ethyl cellulose and 5 g of stearic acid in 25 ml of chloroform and mixing with 90 g of purified menhaden oil. Chloroform is evaporated overnight at 40° C. under nitrogen.

An aqueous core solution, which is preferably a mixture of vitamins and minerals, is combined with lipid wall material and homogenized to form an aqueous-in-lipid emulsion. In the studies described below, 1 g of an aqueous core solution at 40° C. was added to 3 g of lipid wall material at 40° C. and homogenized for 1–2 min. using and Ultra-Turrax T25 available from Ika Wok of Cincinnati, Ohio, to form the aqueous-in-lipid emulsion. The emulsion is then allowed to harden. The hardening can occur at 5° C. for 15 minutes.

In the studies reported below, an emulsifier solution was prepared by dissolving 2.5% (w/w) acacia (gum arabic) in 1M $CaCl_2$. A secondary emulsion was formed by mixing the aqueous-in-lipid emulsion 4–5 times (5 ml each) in hot (60°–70° C.) acacia solution. After each mixing, the suspension was poured into 250 ml of chilled (5° C.) deionized water. Hardened lipid-walled capsules were allowed to separate overnight in a separatory funnel at 5° C. The capsule slurry was collected on a 5 μm mesh nytex filter and stored as a moist slurry in a refrigerator until used.

It should be understood that the amount of ethyl cellulose and saturated fatty acids used for lipid wall materials can vary depending on the hardness of the LWC desired. The amounts of these two components used for lipid wall can change significantly the stability and digestibility of the LWC. Fat soluble vitamins and hormones can also be included in the wall materials. The lipid-walled microcapsule may be formed from lipids including animal, plant, microbial and synthetic oils, phospholipids, and glycolipids and their full/partial hydrolyzed products as well as their derivatives.

In addition, it should be understood that the aqueous core composition can vary significantly depending upon the application of the complex protein-walled capsules of the present invention. In larval fish diets, it is advantageous to utilize minerals and vitamins which will be retained in the LWC for extended periods of time in the presence of water in aquaculture. However, other applications may required the incorporation of different solutions. For example, various pharmaceuticals, drugs, antibiotics, or the like may also be similarly included in the LWC. In a particular aquaculture application, pharmaceutical drugs might be combined with dietary supplements in the LWC, such that the complex protein-walled capsules could both nourish marine larvae and treat any disease or infectants present in the culture.

Preparation of Complex Protein-Walled Capsules

In the studies described below, complex protein-walled capsules (CPWC) were prepared by incorporating LWC containing vitamins and minerals into cross-linked protein-walled capsules. The cross-linking procedure may be similar to that described in Jones et al., *10th European Symposium on Marine Biology*, Belgium, Sep. 17–23, 1975, Vol. 1:127–141, Universal Press, Wetteren, Belgium, or Langdon, *Marine Biology*, 102:217224 (1989). In the studies reported below 4 g of casein was dissolved in 100 ml of 0.02M NaOH solution containing 0.2% (w/v) urea. Casein was used as the protein material due to its widespread use in feeding trials as a standard source of protein; however, it should be understood that other proteins could also be used within the practice of this invention (e.g., hemoglobin, albumin, zein, and other animal/plant proteins). Inclusion of the small amount of urea had the advantage of eliminating clumping of capsules during preparation, and after freeze drying or rehydration.

In the studies reported below 4–5 g of LWC and 10 g of dietary material (menhaden meal, starch and attractants)

were added to the casein solution and mixed thoroughly. An organic solvent was prepared by dissolving 1% (v/v) adipoyl chloride and 2% (w/v) crude soy lecithin in 250 ml of cyclohexane. Solvents other than cyclohexane, and cross-linking agents other than adipoyl chloride may be used within the practice of this invention, and should be chosen depending upon the nature of the protein-walled microcapsules desired.

The casein/diet mixture was atomized through a pressurized (20 psi $N_2$) nozzle unit (Wheaton Thin Layer Chromatography Sprayer) into the organic solution (cyclohexane). FIG. 1 shows a schematic diagram of a gas-nozzle atomizing unit used in the preparation of the complex protein-walled capsules of the present invention. The feedstuff, casein and LWC mixture 10 stored in stoppered vessel 12 is directed up through the conduit 14 via pressure from $N_2$ gas fed into the vessel through side arm 16. At the atomizer 18, additional $N_2$ gas, directed through conduit 20, becomes entrained with the mixture, and a fine spray of microparticles 22 is created. The size of the atomized particles is controlled using valves 24 and 26 which regulate the $N_2$ gas flow to the mixture in vessel 12, and the flow of $N_2$ gas to be entrained. Microcapsules 28 are formed in the cyclohexane, lecithin and adipoyl chloride solution 30. Ideally, the solution is swirled continuously using a stir bar 32 and stir plate 34.

The above-described procedure allowed a rapid encapsulation of the LWC in the cross-linked protein-walled capsules before dissolving in cyclohexane. The capsule suspension was allowed to harden for 20 minutes, and the microcapsules were allowed to settle in the beaker 36. The supernatant was decanted and the capsules were poured into fresh cyclohexane. The remaining adipoyl chloride was washed several times with fresh cyclohexane. Finally, the capsules were freeze-dried, and dry sieved through 300 μm and collected on 70 μm mesh nytex filters.

Size Distribution of LWC and CPWC

The size distribution of LWC and CPWC prepared according to the procedures described above was determined in a pre-calibrated multichannel particle counter (Coulter Counter TAII, available from Coulter Electronics) at 280 and 560 μm aperture opening, respectively. Approximately 5–10 mg of LWC and CPWC were hydrated in 200 ml of Isotone® solution. Size distribution was measured at 10 second intervals and expressed as a percentage of the total count.

Release of Lysine and $^3$H-leucine from LWC, PWC, and CPWC

Crystalline amino acid lysine (non-labeled) and $^3$H-leucine were chosen to determine the leaching rate of low molecular weight (LMW) nutrients from microencapsulated diets because they are highly water soluble and are essential for marine and fresh water fish. The LWC were prepared as described above, and by dissolving 100 mg of lysine in 1 ml of distilled water for use as the aqueous core solution. The LWC were washed three times with 100 ml deionized water to remove the unencapsulated lysine. $^3$H-leucine was encapsulated in the same manner as lysine. The CPWC were prepared by incorporating the LWC containing lysine or $^3$H-leucine into the cross-linked casein-walled capsules. Conventional protein-walled capsules (PWC) were prepared by encapsulating 100 mg of lysine or $^3$H-leucine in the cross-linked protein wall membrane using 10 ml of casein solution.

Release of lysine was determined from LWC, PWC, and CPWC using the ninhydrin reaction described in Doi et al., *Analytical Biochemistry*, 118:173–184 (1989). Fifty microliters of sample was placed in a microtiter plate well and added with 150 μl of ninhydrin reagent containing 0.8 g ninhydrin in 80 ml of ethanol (95%), 10 ml of glacial acetic acid, and 1 g/ml $CdCl_2$. Purified lysine was used as a standard and was applied to the plate along with the samples. The plate was incubated at 85° C. for 10 minutes and absorbance was read at 540 nm in a microtiter plate reader (Titertek available from ICN Biomedicals).

Approximately 100 mg wet weight of LWC containing 150 μg of lysine per mg wet weight was added on a 1×25 cm glass chromatography column containing 10 ml of deionized water. The column was gently mixed for a few seconds to provide an even distribution of LWC. The LWC were allowed to float for 30 min and 1 ml of LWC free water was removed from the bottom of the column plugged with cotton wool. This was designated as $t_0$. One ml aliquot was removed from the column at $t_{24h}$ and 50 μl was used for determination of lysine. The difference between $t_0$ and $t_{24}$ indicated the amount of lysine released from the LWC. The release rate of lysine was expressed as percentage of total lysine contained in capsules added to the water column.

Release of lysine from PWC and CPWC was determined for 2 h after immersion in water. Prior to the encapsulation of lysine, ninhydrin positive substances were removed by washing the casein with 80% (v/v) ethanol. PWC and CPWC were prepared as described above. Five mg of PWC or CPWC containing 236 and 30 μg lysine, respectively, were placed in a microcentrifuge tube and 1 ml of deionized water was added. The capsule suspensions were hand shaken and centrifuged for 1 min. at 1,000 rpm using an Eppendorf microcentrifuge. Fifty μl of supernatant was removed at 0, 5, 15, 30, 60 and 120 min. after hydration of the freeze-dried CPWC and PWC for the detection of lysine. The capsule suspensions were kept in a shaker during the experiment. Total lysine content of the capsules were determined after the disruption of the capsules in a homogenizer and a sonicator bath. The release of lysine was expressed as a percentage of the total lysine present in the capsules.

The $^3$H-leucine labeled capsules were treated in a manner similar to lysine labeled capsules, and the release rates from LWC, PWC, and CPWC were determined using a liquid scintillation counter.

In Vitro Digestibility of Complex Protein-Walled Capsules

In vitro digestibility of CPWC was determined using purified pepsin (porcine stomach mucosa), trypsin (porcine pancreas), or a crude enzyme extract prepared from 20 day old striped bass larvae. A batch of CPWC containing no free amino acids and casein as the only source of wall material were prepared to determine the breakdown of cross-linked protein wall of the capsules. Five mg. of freeze dried PWC free of amino acids was suspended in 1 ml of 0.1M acetate buffer, pH 5.0, and 0.1M of Tris buffer, pH 8.0 for peptic and tryptic digestion, respectively. Various concentrations (0, 0.5, 1, 2, and 4 mg) of bovine pancreatic pepsin or trypsin were added in the suspension and incubated for 1 hour at room temperature. Digestibility was determined as μg amino acid produced (lysine equivalent) per hour using ninhydrin reagent. Blank incubations omitting the enzymes were run in parallel for all in vitro assays as controls.

Approximately 250 mg wet weight of striped bass *Morone saxatilis* larvae (20 days post hatching) were homogenized in 0.1M Tris buffer, pH 7.0. The homogenate was centrifuged for 30 min. at 20,000 g, and supernate was used for the assays. Enzyme extract in various quantities (0,0.2, 0.4, 0.8 and 1.6 mg protein) were added to 5 mg/ml PWC suspension in the same buffer. The incubation was carried out for 20 hours. Proteolytic digestion was determined as µg amino acid produced per hour (lysine equivalent) using ninhydrin reagent. The reaction was linear up to 24 hours ($R^2$=0.97).

Digestibility of CPWC by 13 days post-hatching larvae was also observed microscopically using an Olympus BH2 microscope equipped with SC-35 Olympus camera. Photomicrographs were taken at 40x.

Data Analysis

All assays were conducted at least in triplicate. Data were expressed as mean±standard error. One way ANOVA was employed to determine the effects of microcapsule type on the release of lysine. Regression analysis was conducted using SYSTAT statistical package.

Results

Size Distribution and Encapsulation Efficiency

The atomization unit designed for the gas-nozzle extrusion of microparticles shown in FIG. 1 was effective in the production of complex protein-walled microcapsules. Over 80% of the protein-walled capsules were between 130–200 µm in size with a mean diameter of 153 µm. Preferably, the size of microparticles used for the diet of marine and shellfish larvae will be less than 250 µm. As discussed above in connection with FIG. 1, valves 24 and 26 can be adjusted to entrain more or less gas for atomization, depending upon whether smaller or larger microparticles are desired. The lipid-walled capsules prepared as described above had a wider range of size with a mean diameter of 35 µm. The LWC had both singular and multiple aqueous core droplets embedded in a lipid/ethyl cellulose matrix.

The process facilitated rapid encapsulation of the LWC in the cross-linked protein-walled capsules before partitioning of the lipids into the cyclohexane phase. The encapsulation efficiency of lysine into LWC was calculated from the lysine content of the upper methanol/water phase after the extraction of the LWC paste with chloroform:methanol:water (2:2:1 by volume). Aqueous cores of LWC formed 18.9% (±1.6 w/w) of total capsule. Approximately 63% of the initial aqueous material was encapsulated in LWC as determined by liquid scintillation counting of encapsulated $^3$H-leucine after filtration on glass fiber filters (0.45 µm).

Release of Lysine from Capsules

Figure 2:
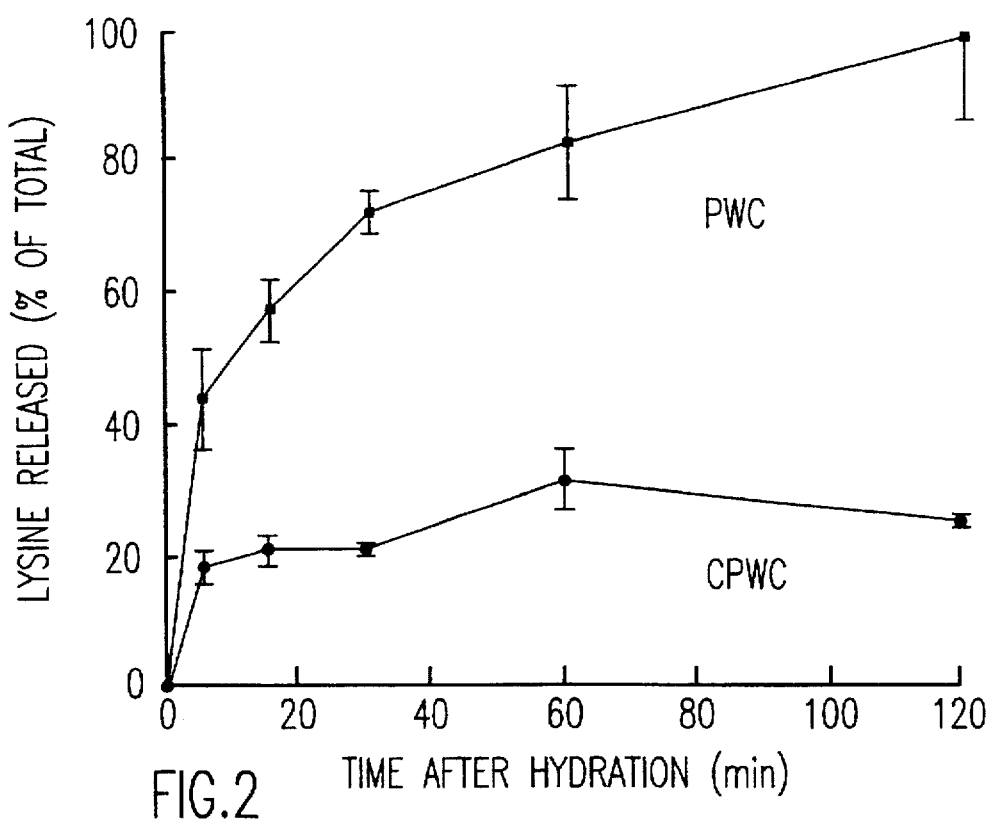
FIG. 2 is a graph showing the release rate of lysine from protein-walled capsules and from complex protein-walled capsules.

Release kinetics of both labeled and unlabeled amino acids were similar. FIG. 2 shows the release of lysine from conventional PWC and CPWC. Nearly 45% of the total lysine leached out of PWC 5 min. after hydration. The loss of lysine steadily increased with time, reaching 70% and 99%, 30 min. and 2 hours after hydration, respectively. In sharp contrast, lipid-walled capsules retained >90% of their lysine content after 24 hours. The release of lysine from CPWC was significantly lower (p<0.05) than that observed for PWC. Approximately 20% of the total lysine was released into water at 15–20 min. after hydration, and the rate of release remained relatively constant thereafter (>30% after 2 hours).

In vitro digestibility

Figure 3:
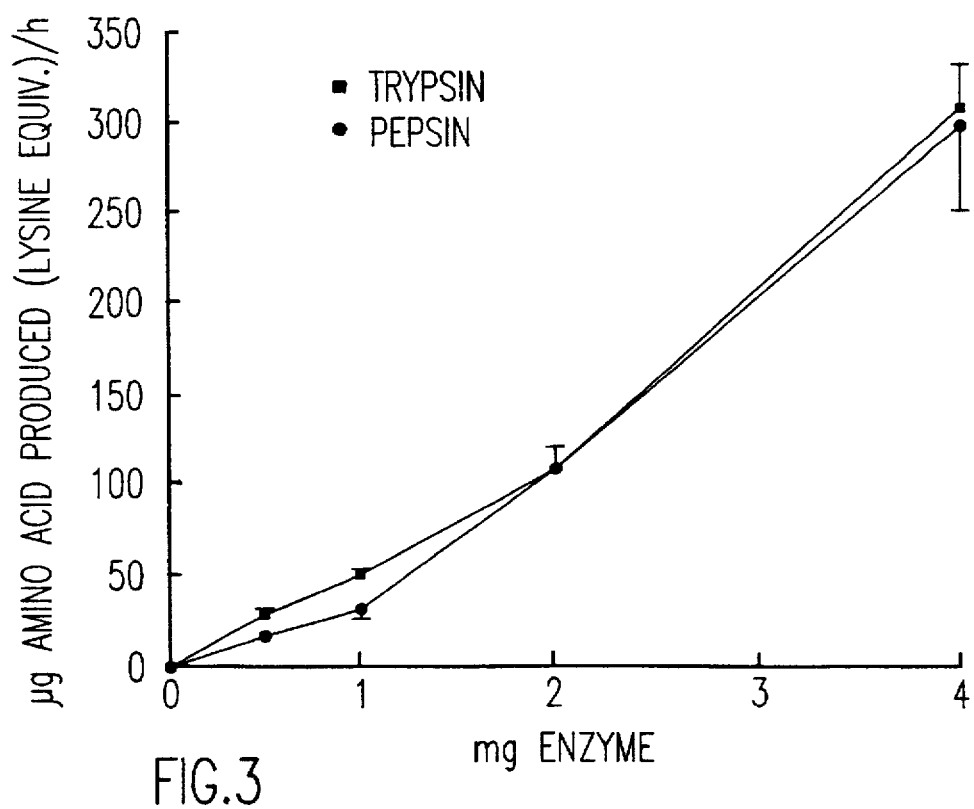
FIG. 3 is a graph showing the accumulation of free amino acids in capsule suspensions with trypsin and pepsin.
Figure 4:
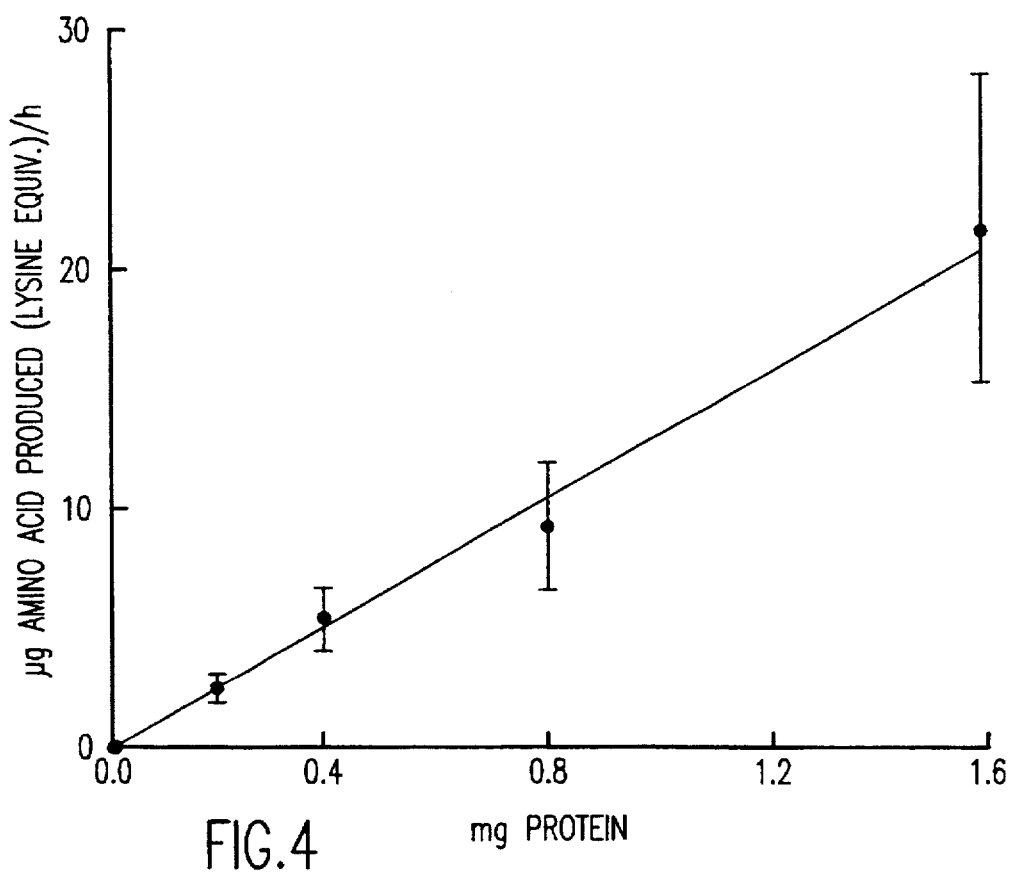
FIG. 4 is a graph showing the accumulation of free amino acids in capsule suspension with a crude enzyme extract from striped bass larvae.

Assays using crude enzyme extracts from 20 days post-hatching striped bass larvae or purified porcine trypsin and pepsin indicated that CPWC were susceptible to in vitro enzymatic digestion. FIG. 3 shows incubation of CPWC with various amounts of pepsin or trypsin resulted in increased accumulation of free amino acids in capsule suspensions. Both the tryptic and peptic digestion produced the same amount of amino acids, and the reactions were generally linear with time ($R^2$=0.97, 0.98). FIG. 4 shows crude enzyme extract from striped bass larvae was capable of breaking down the cross-linked protein wall. The rate of breakdown increased linearly ($R^2$=0.99) with the increased amounts of enzyme protein in the suspensions.

Conclusions

The above described studies demonstrate that the complex microencapsulated diet can effectively retain low molecular weight, highly water soluble nutrients (e.g., lysine, leucine) within 24 hrs of immersion in water. Comparatively, the CPWC released only 25% of their lysine content after 2 hours, while 100% release occurred with PWC in the same time period. High molecular weight compounds, such as proteins, are known to be efficiently retained (>95%) in protein-walled capsules when suspended in seawater for 24 hours. A gradual release of low molecular weight phagostimulants is desirable to evoke ingestion in fish larvae, while efficient retention of other nutrients is necessary to preserve the nutritional quality. Therefore, CPWC is ideal for nutrient delivery to fish larvae. Examples 1 and 2 below confirm the utility of CPWC in nutrient delivery to fish larvae and show that 75% of the larvae accepted the diet as first food. Microscopical examination of the larvae also revealed that the CPWC were being digested in the anterior section of the digestive tube.

Figure 5:
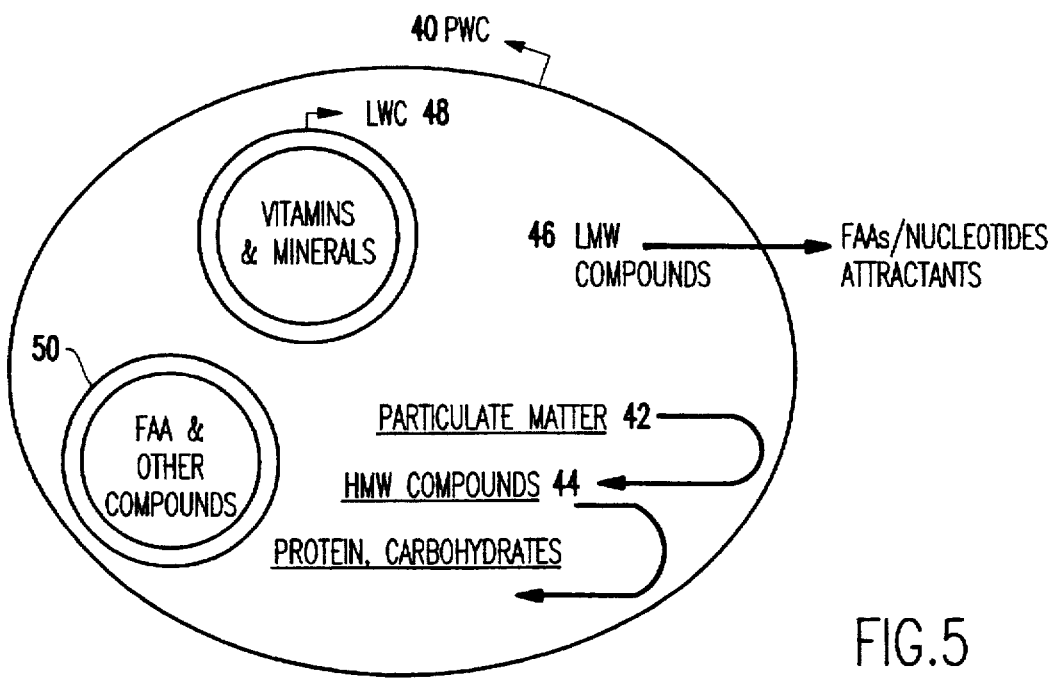
FIG. 5 is a schematic drawing of one type of complex microcapsule according to the present invention.

FIG. 5 shows a model for a microencapsulated diet for larval fishes. In this model, the outer shell of the microcapsule is a cross-linked protein-walled capsule 40. The protein employed for formation of the capsule 40 can be casein, hemoglobin, albumin, zein and/or other animal/plant proteins. In a fish diet, preferably the protein employed is one that will be accepted by the fish and will offer nutrient value. Particulate matter 42 and high molecular weight compounds 44, such as proteins and carbohydrates, can be added together with the protein used to form the capsule at the time of capsule formation, and can be used as a source of additional nutrients for the fish larvae. Due to the cross-linked character of the protein capsule, the particulate matter 42 and high molecular weight proteins do not easily leach out upon hydration, and thus, they are retained as a nutritive source upon ingestion. The semi-permeable nature of protein membrane 40 is an important feature that allows the release of LMW attractants 46, such as free amino acids and nucleotides, that trigger ingestion by fish larvae. Highly water soluble compounds, such as vitamins and minerals, however, are encapsulated in the lipid wall capsules 48 which do not leach out these essential nutrients, thus preserving the nutritional quality of the diet. Additionally, the capsule 40 can also include encapsulated digestive enzymes, free amino acids, and other compounds in capsules 50.

The complex nature of the CPWC, which allows release of different materials at two different release rates in hydrating environments, may find use in other applications such as drug delivery, etc. Specifically, a first compound which is readily soluble in water that is relatively small in size such that it can penetrate through a cross-linked protein membrane would be selected for incorporation into the PWC 40. A second compound, which may or may not be the same as the first compound, which is to be retained, is selected for incorporation into the LWC 48. As explained above, the CPWC is formed by combining a non-crosslinked protein, LWCs with associated materials (e.g., vitamins and minerals), and other materials of interest for incorporation into the PWC (e.g., carbohydrates, high molecular weight compounds, other proteins, and particulates) together in a mixture. The mixture is then atomized by directing it through a spray nozzle or other device. While in the form of microparticles, the protein which forms the PWC is rapidly crosslinked. In the test studies described above, crosslinking was achieved by collecting the microparticles in a solution containing a cross-linking agent. However, it should be understood that other methodologies for crosslinking may be used (e.g., exposing the microparticles to ultraviolet or radiant energy, thermal processing, etc.).

Additional complex protein microcapsules can be formed by drying, denaturing or desolving the protein components. These methods may include spray drying protein component, denaturing the protein by heat or exposing to a denaturing solvent, or allowing the protein to come out of solution (desolving) by solvent/solvent incompatibility. After these procedures, the protein microparticles can be crosslinked. The microcapsules produced from this methodology still have a complex nature.

EXAMPLE 1

A complex microencapsulated diet which incorporates lipid-walled capsules that contain water soluble nutrients (vitamins and minerals) into cross-linked protein-walled capsules was prepared according to the methodology described above. Casein and hemoglobin were used to prepare the protein walled capsules, while lipid walled capsules were prepared from menhaden oil. The protein walled capsules comprised menhaden fish meal, potato starch and soy lecithin. Total protein and lipid contents of the encapsulated diet were 53% and 23% of dry weight, respectively. The size of the complex protein walled microcapsules were in the range of 80–300 µm. Glycine, betaine, inosine and inosine 5'-monophosphate were included as the attractants. The ingestion rates (percent of larvae with diet in their guts) of hemoglobin-walled (HWC) and casein-walled (CWC) microcapsules by 7 days post hatching (DPH) striped bass larvae were 40% and 4%, respectively. At 14 DPH, the ingestion rate increased to 75% for HWC and 100% for CWC. When CWC was modified to include water and lipid soluble fractions of Artemia, the ingestion rate was improved to 75% for 7 DPH (it retained an ingestion rate of 100% for 14 DPH). Microscopic examination of the larval digestive tract indicated that modified CWC was digested within 4–6 hours.

EXAMPLE 2

In two separate experiments 7 DPH, striped bass larvae were fed complex microencapsulated diets in full or partial replacement of the live food *Artemia nauplii*, for two weeks. In Experiment 1, treatments comprised HWC (1.1 mg/larvae/day), CWC (1.1 mg/larvae/day), Artemia (2 nauplii/ml)+HWC (1.1 mg/larvae/day), and Artemia (2 nauplii/ml)+CWC (1.1 mg/larvae/day). In Experiment 2, the treatments comprised modified CWC that contained water and lipid soluble fractions of Artemia (1.1 mg/larvae/day), or modified CWC supplemented with Artemia (2 nauplii/ml +1.1 mg/larvae/day). In Experiment 1, the ingestion rates of HWC and CWC were 40% and 46%, respectively. HWC did not support growth and survival when solely fed to the larvae and 100% mortality was recorded after 17 DPH. CWC fed larvae, by contrast, showed a 8.7% survival rate at the end of the experiment, 20 DPH, but no growth was observed. Partial replacement (60%) of Artemia with both HWC and CWC significantly ($P<0.05$) increased the wet weight of the larvae. The mean weight of the larvae fed Artemia supplemented with CWC was similar to that of the larvae fed a full ration of Artemia, and was significantly higher than that of larvae fed a 40% ration of Artemia. In Experiment 2, the ingestion rate of modified CWC was significantly improved (49%), while wet weight did not show any significant increase. Supplementing the live food CWC significantly increased the growth of larvae compared to that of the non-supplemented control (40% ration Artemia). The results of this study suggest that CWC can be used for partial replacement of live food without any significant effect on the growth and survival of striped bass larvae.

While the invention has been described in terms of its preferred embodiments, those skilled in the art will recognize that the invention can be practiced with modification within the spirit and scope of the appended claims.

We claim:

1. A method for forming complex protein-walled microcapsules, comprising the steps of:

combining a lipid-walled microcapsule incorporating a first constituent with a second constituent that is not incorporated in said lipid-walled microcapsule, and a protein to form a mixture;

forming microparticles from said mixture which include said lipid-walled microcapsule and said second constituent incorporated in said protein, said forming step including the step of atomizing said mixture; and cross linking said protein in said microparticles to form a protein microcapsule which incorporates said lipid-walled microcapsule and said second constituent.

2. The method of claim 1 wherein said step of atomizing includes the steps of:

directing said mixture to a spray nozzle; and entraining a gas in said mixture at said spray nozzle.

3. A method for forming complex protein-walled microcapsules, comprising the steps of:

combining a lipid-walled microcapsule incorporating a first constituent with a second constituent that is not incorporated in said lipid-walled microcapsule, and a protein to form a mixture;

forming microparticles from said mixture which include said lipid-walled microcapsule and said second constituent incorporated in said protein; and exposing said microparticles to ultraviolet or radiant energy, said exposing step crosslinking said protein to form a polymer microcapsule which incorporates said lipid-walled microcapsule and said second constituent.

* * * * *